(12) United States Patent
Staehr et al.

(10) Patent No.: US 7,256,888 B2
(45) Date of Patent: Aug. 14, 2007

(54) FLUID VERIFICATION SYSTEM AND METHOD FOR INFUSIONS

(75) Inventors: Linda B. Staehr, Vista, CA (US); James L. Cudney, Santee, CA (US); Roger J. Greenwald, San Diego, CA (US)

(73) Assignee: Cardial Health 303, Inc., San Diego, CA (US)

( * ) Notice: Subject to any disclaimer, the term of this patent is extended or adjusted under 35 U.S.C. 154(b) by 321 days.

(21) Appl. No.: 10/704,063

(22) Filed: Nov. 7, 2003

(65) Prior Publication Data

US 2005/0099624 A1    May 12, 2005

(51) Int. Cl.
*G01J 3/42*    (2006.01)

(52) U.S. Cl. .................................. 356/319; 356/325

(58) Field of Classification Search ................ 356/319, 356/323, 325, 326, 328
See application file for complete search history.

(56) References Cited

U.S. PATENT DOCUMENTS

| | | |
|---|---|---|
| 3,734,601 A | 5/1973 | Heiss |
| 4,086,058 A | 4/1978 | Pendleton |
| 4,409,966 A | 10/1983 | Lambrecht et al. |
| 4,717,545 A | 1/1988 | Morris |
| 4,888,484 A | 12/1989 | Harvey |
| 5,468,224 A | 11/1995 | Souryal |
| 5,491,344 A | 2/1996 | Kenny et al. |
| 5,510,621 A | 4/1996 | Goldman |
| 5,681,285 A | 10/1997 | Ford et al. |
| 5,900,934 A | 5/1999 | Gilby et al. |
| 5,910,776 A * | 6/1999 | Black ........................ 340/10.1 |
| 6,111,639 A | 8/2000 | Reduto |
| 6,122,042 A | 9/2000 | Wunderman et al. |
| 6,262,340 B1 | 7/2001 | Betlach et al. |
| 6,307,625 B1 | 10/2001 | Sharts et al. |
| 6,445,449 B1 | 9/2002 | Sharts et al. |
| 2003/0204331 A1 | 10/2003 | Allgeyer |

FOREIGN PATENT DOCUMENTS

WO    WO 02/11049 A2    2/2002

OTHER PUBLICATIONS

A R Boyd, S E J Bell, and A C Dennis; *Raman Spectroscopy for Future Drug Discovery*; Technology & Services, Avalon Instruments Ltd., Northern Ireland, UK; pp. 1-6, no date.

Stephen J. Matthews, *The many variations of the Raman effect*; Laser Focus World, Sep. 2003; pp. 89-93.

\* cited by examiner

*Primary Examiner*—F. L. Evans
(74) *Attorney, Agent, or Firm*—McDermott Will & Emery (57) ABSTRACT

An apparatus and method are provided to verify the composition of a medical fluid in a fluid infusion channel by comparison with clinician-entered input. Light is transmitted through the channel and detected by a sensor that generates signals representative of the spectral data of the light detected. A processor compares the spectral data of the light detected to the spectral data associated with the expected contents of the channel to verify that the correct fluid is being infused.

36 Claims, 6 Drawing Sheets

FLUID VERIFICATION SYSTEM AND METHOD FOR INFUSIONS

BACKGROUND OF THE INVENTION

The invention is related to the verification of the contents of a fluid, and more particularly, to the analysis of a medical fluid for verifying the existence of a pharmaceutical drug or drugs to be infused into a patient through a fluid infusion channel.

Physicians and other medical personnel apply intravenous ("IV") infusion therapy to treat various medical complications in patients. IV infusion therapy typically involves infusing medical fluids, such as pharmaceutical drugs, from a fluid source through the tubing of a fluid administration set, and to a cannula inserted in a patient's blood vessel.

In a typical facility, a physician enters an order for a medication for a particular patient. This order may be handled either as a simple written prescription slip, or it may be entered into an automated system, such as a physician order entry ("POE") system. The prescription is routed to the pharmacy, where the order is filled. Typically, the prescribed drug is prepared and inserted into a bag at the pharmacy. A pharmacist also identifies the contents of the bag and the patient for whom the bag is intended, with, for example a human-readable label and a bar coded label. The prepared medication is then delivered to a clinician's station for subsequent administration to the patient.

For safety reasons, and in order to achieve optimal results, the pharmaceutical drug is administered in accurate amounts as prescribed by the doctor, and in a controlled fashion such as by using an infusion pump. An infusion pump moves fluid from the medical fluid bag through a fluid infusion channel and into the patient. The infusion pump is programmed by a medical clinician according to the particular pumping or infusion parameters prescribed by the doctor. The pumping parameters programmed into the pump by the clinician are drug and patient specific. That is, the pumping parameters are selected by the doctor based on the particular drug prescribed and the specific patient for whom it is intended. It is the clinician's responsibility to match the prescribed drug with the correct patient and with the properly programmed pump.

Hospitals and other institutions continually strive to provide quality patient care. A medical error, such as when a patient receives the wrong drug, is a significant concern for all heath care facilities. In some cases, a single patient may be prescribed simultaneous multiple infusions, sometimes four or more, of different drugs. Typically, multiple infusions involve different infusion parameters for each drug. Further, such multiple infusions may involve multiple pump channels; e.g., one channel for each infusion; or a secondary to a primary infusion. Some pump systems include four or more pumping modules, each of which comprises an infusion pump operating on a separate fluid tubing to form a separate pumping channel. Regardless of whether a system has multiple channels or multiple systems each having only one channel, it is important that each channel be correctly programmed to infuse the right drug into the patient. Installing the tubing from a pharmaceutical bag into an incorrect pumping module could result in the wrong drug being pumped into the patient, regardless of correct drug labeling.

Prior attempts have been made to assure that the right drug is administered to the right patient through the right channel. In one example, a bar code label identifying the drug and patient is applied to the bag at the pharmacy. After a clinician manually programs the pump, a bar code scanner connected to the pump is used to read the bar code label on the bag to verify that it identifies the same medication as that programmed. In another example, a bar code label is applied to the bag and the label is read with a bar code scanner to automatically program the pump, thus avoiding manual programming entirely. While doctors are more assured that the doses and infusion rates that they prescribe can be delivered to the patients accurately by the pumps available today, such as via the MEDLEY™ patient care system operating the GUARDRAILS® safety system, there remains a concern that the right drug is mounted to the right pump.

Even though the pump systems of today provide significant advances in the art to avoid medication errors, there is a desire to more reliably determine that the correct drug is being infused. For example, the pharmacist may have made a mistake in mixing the component fluids for the bag, or the pharmacist may have applied the wrong bar code label to the bag. The bar code could also contain incorrect information or the clinician could scan the bar code label of the correct bag, but become distracted especially during emergency situations or MEDVAC (helicopter transport for example), and connect the tube from the bag to the wrong pumping channel.

Hence, those skilled in the art recognize that a need exists to more accurately ensure that the correct drug or combination of drugs is properly infused into the correct patient. More particularly, those in the art have recognized a need to more definitely ascertain that the particular pharmaceutical drug a pump is infusing into the patient is the correct drug in the correct concentration. The present invention fulfills these needs and others.

INVENTION SUMMARY

The present invention is directed to a system and method for verifying the contents of a fluid in a conduit. With more particularity, an apparatus is provided for verifying the composition of a fluid contained within a fluid infusion conduit, wherein the conduit includes a conduit wall and an interior through which the fluid is conducted, the apparatus comprising a source of light located and configured so as to direct light through the fluid contained within the conduit, a light sensor located so as to receive the light that was directed through the fluid contained within the conduit after it has passed through the fluid, the light sensor providing light sensor signals representative of a spectrum of the actual composition of the fluid contained within the conduit, and a processor that is adapted to compare the spectrum of the actual composition of the fluid with a spectrum of an expected composition of the fluid contained within the conduit.

In further aspects, a memory is provided in which is stored the spectrum of the expected composition of the fluid contained within the conduit wherein the processor accesses the memory to obtain the spectrum of the expected composition of the fluid contained within the conduit. An input device is also provided with which an indication of the expected composition of the fluid is input to the processor. In a further aspect, the conduit is operated on by a pumping mechanism of an infusion pump wherein the source of light and the light sensor are disposed at locations on the infusion pump upstream from the pumping mechanism.

In yet further aspects, the apparatus further comprises a reference element indicative of a spectrum of the conduit wall, a source of light is located and configured so as to direct light through the reference element, and a light sensor is located so as to receive light that was directed through the reference element after it has passed through the reference element, the light sensor providing light sensor signals representative of a spectrum of the actual composition of the reference element wherein the processor is further adapted to adjust the spectrum of the actual composition of the fluid within the conduit with the spectrum of the actual composition of the reference element.

In further aspects, a predetermined spectrum is representative of the composition of the conduit wall wherein the processor is further adapted to adjust the spectrum of the actual composition of the fluid within the conduit with the predetermined spectrum representative of the conduit wall. In other aspects, the apparatus further comprises a memory in which is stored a plurality of spectra of possible expected fluid compositions contained within the conduit, an input device with which the expected composition of the fluid contained within the fluid conduit is input to the processor, wherein in response to the input device the processor accesses the memory to obtain the spectrum of the expected composition of the fluid contained within the conduit. In another aspect in accordance with the invention, the processor is adapted to access additional spectra in the memory in the event that the spectrum of the expected composition does not match the spectrum of the actual composition and make further comparisons of spectra from the memory to the spectrum of the actual composition, and in the event that a match is detected, indicates the spectrum that matched. In a further aspect, the processor is further adapted to synthesize a spectrum for the expected fluid composition from spectra in the memory.

In another aspect, the processor is further adapted to provide an alarm signal in the event that the spectrum of the actual composition does not match the spectrum of the expected composition. Yet further, the processor controls the pumping mechanism and is adapted to prevent the pumping mechanism from operating in the event that the spectrum of the actual composition does not match the spectrum of the expected composition. The processor is further adapted to permit an operator of the pump to override the processor in the event that the spectra do not match. The apparatus further comprises a memory wherein the processor is further adapted to store in the memory an override of the processor. The processor is further adapted to communicate with a hospital server located remotely from the processor events relating to comparisons of spectra.

In more detailed aspects, the apparatus further comprises a reader device in communication with the processor adapted to read an identification device related to the fluid, the identification device including an indication of expected composition of the fluid. The identification device contains a spectrum of the expected composition of the fluid. The identification device contains an indication of the expected fluid composition and the processor is adapted to retrieve a spectrum consistent with the expected fluid composition. The identification device comprises a bar code and the reader comprises a bar code scanner. In another aspect, the identification device comprises an RFID tag and the reader comprises an RFID reader. In yet further detailed aspects, the identification device comprises a wireless information device and the reader comprises a compatible reader of the wireless information device.

In accordance with the method in accordance with aspects of the invention, there is provided a method for verifying the composition of a fluid contained within a fluid infusion conduit, wherein the conduit includes a conduit wall and an interior through which the fluid is conducted, the method comprising directing light through the fluid contained within the conduit, sensing the light that was directed through the fluid contained within the conduit after it has passed through the fluid and providing light sensor signals representative of a spectrum of the actual composition of the fluid contained within the conduit, and comparing the spectrum of the actual composition of the fluid with a spectrum of an expected composition of the fluid contained within the conduit.

In more detailed aspects, the method further comprises storing the spectrum of the expected composition of the fluid contained within the conduit in a memory, and accessing the memory to obtain the spectrum of the expected composition of the fluid contained within the conduit. In other detailed aspects, the method comprises directing light through a reference element, receiving light that was directed through the reference element after it has passed through the reference element, the received light being representative of a spectrum of the actual composition of the reference element, and adjusting the spectrum of the actual composition of the fluid within the conduit with the spectrum of the actual composition of the reference element.

In other aspects, the method further comprises receiving a predetermined spectrum representative of the expected composition of the conduit wall, and adjusting the spectrum of the actual composition of the fluid traveling through the conduit with the predetermined spectrum representative of the conduit wall. The method additionally may comprise storing a plurality of spectra of possible expected fluid compositions contained within the conduit, inputting the expected composition of the fluid contained while within the fluid conduit, and accessing the spectrum of the expected composition of the fluid contained within the conduit from the plurality of spectra. Further, the method comprises accessing additional spectra in the event that the spectrum of the expected composition does not match the spectrum of the actual composition and further comparing spectra to the spectrum of the actual composition, and in the event that a match is detected, indicating the spectrum that matched. Additionally, the method comprises synthesizing a spectrum for the expected fluid composition from spectra to identify a drive.

In yet other detailed aspects, the method further comprises providing an alarm in the event that the spectrum of the actual composition does not match the spectrum of the expected composition. The method further comprises reading an identification device related to the fluid, the identification device including an indication of expected composition of the fluid. The method further comprises reading an identification device that contains a spectrum of the expected composition of the fluid. The method further comprises reading a bar code identification device with a bar code scanner. The method further comprises reading an RFID tag with an RFID reader. The method further comprises reading a wireless information device with a compatible reader.

Other aspects and advantages of the invention will become apparent from the following detailed description and the accompanying drawings, illustrating by example the features of the invention.

DETAILED DESCRIPTION OF THE PREFERRED EMBODIMENTS

Figure 1:
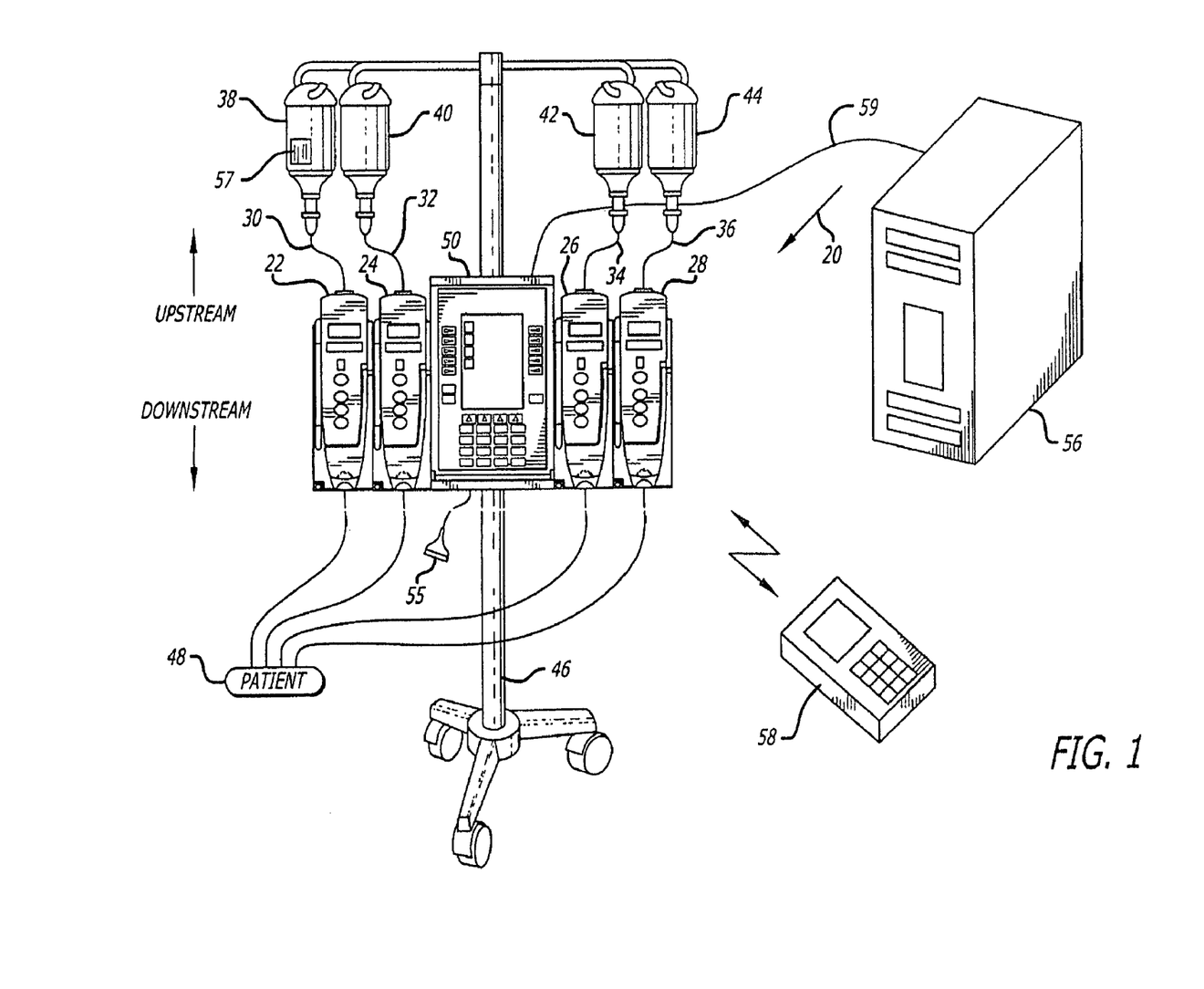
FIG. 1 is a view of a system in accordance with aspects of the invention showing a medical instrument having four medical fluid infusion pumps connected to respective fluid sources and a single patient through respective fluid administration sets. A programming module is connected to all pumps and is shown as having a connection to a remote processor through a communication link. Further, a portable device is shown to communicate with the medical instrument through a wireless link, although a different connection is possible.

Referring now to the drawings in which like reference numerals refer to like or corresponding elements among the several views, there is shown in FIG. 1, as an example, a patient care system 20 having four infusion pump modules 22, 24, 26, and 28 each of which is in operative engagement with the tubing of a respective fluid administration set 30, 32, 34, and 36. Four medical fluid sources 38, 40, 42, and 44, which may take various forms but in this case are shown as bottles, are inverted and suspended above the patient care system 20. The patient care system 20 and the bottles 38, 40, 42, and 44 are mounted to a roller stand or IV pole 46. The administration sets 30, 32, 34, and 36 are connected between respective fluid sources and a patient 48 (shown only in block form) so that the patient may receive the fluids in the fluid sources at rates controlled by the respective infusion pump modules. The pumping system shown in FIG. 1 is provided only as an example of a system with which the drug verification system and method of the invention may be used. Other pumping systems and non-pumping systems, such as a gravity feed system, may be usable in accordance with the invention.

It should be noted that the drawing of FIG. 1 is not to scale and that distances have been compressed for the purpose of clarity. In an actual setting, the distance between the bottles 38, 40, 42, and 44 and the infusion pump modules 22, 24, 26, and 28 could be much greater. There would be more of an opportunity for the tubings of the administration sets 30, 32, 34, and 36 to become intertwined with each other when all four are dangling from the bottles, which can cause confusion as to which tubing should be in which infusion module. The opportunity for confusion increases as the number of tubings increases.

Figure 2:
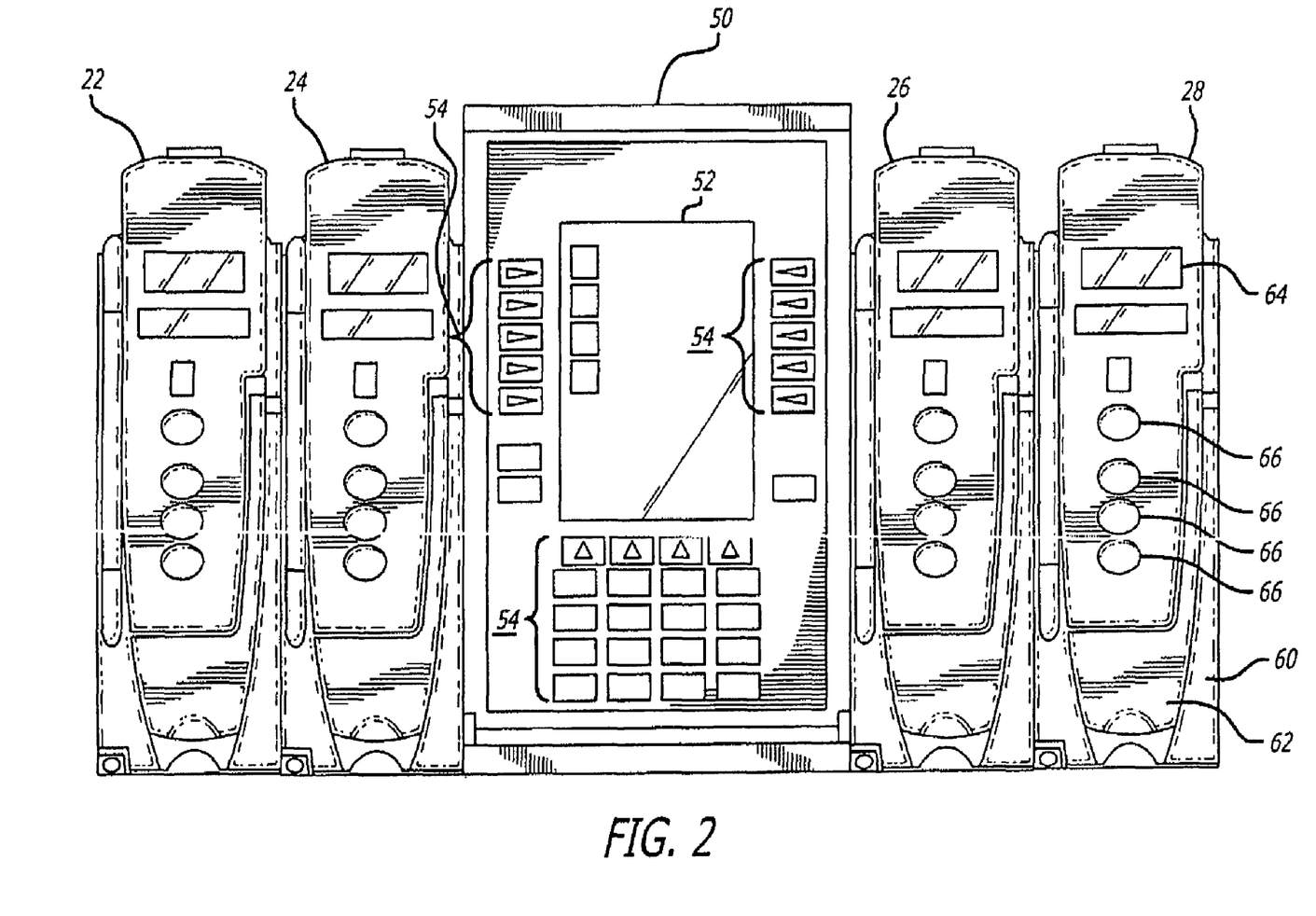
FIG. 2 is an enlarged view of the medical devices of FIG. 1 showing displays and control keys of the fluid infusion pumps attached to the programming module.

Referring now to both FIGS. 1 and 2, a programming module ("PM") 50 is connected to the infusion pump modules 22, 24, 26, and 28. Other devices or modules may be attached to the PM. In one embodiment, the PM is used to provide an interface between the infusion pump modules and external devices as well as to provide most of the user interface for the infusion pump modules. The PM includes a display 52 for visually communicating various information, such as the operating parameters of each of the pump modules as well as displaying alert and alarm messages. The PM may also include a speaker (not shown) to provide audible alarms. The PM also has various input devices in this embodiment including control keys 54. Further details on the PM and on a patient care system such as that shown in FIGS. 1 and 2 may be found in U.S. Pat. No. 5,713,856 to Eggers et al., incorporated herein by reference.

The PM 50 may also include a reader 55 for receiving information relating to the infusions, such as drug identification, patient identification, nurse identification, and other information. An identification device 57 is shown on a fluid container 38 which in this case is a bar code. Likewise, the reader 55 in this case is a bar code scanner. However, the identification device may take other forms such as an RFID tag, a wireless device, or other, but contains an indication of the expected fluid composition. The indication may also include spectrum data consistent with the expected fluid composition, or merely a drug name. Similarly, the reader may comprise an RFID reader or wireless device compatible with the identification device 57. The PM also has a communications system with which it may communicate with a medical facility server 56 or other computer or computers and with a portable digital assistant ("PDA") 58, such as a palm-based system, that a care giver may have so that information may be transferred between such device and the PM and infusion pump modules. Pump programming information may be uploaded into the PM or verified from the PM. The PM may also be used to store drug libraries for use in conjunction with infusion devices as well as vital signs monitoring devices, and for other uses. The communications system between the PM and other devices may take the form of an RF (radio frequency) system, an infrared system, a Blue Tooth system, or other wired or wireless systems. For illustrative purposes, the communications link between the patient care system 20 and the medical facility server 56 is shown as a solid line indicated by numeral 59. The bar code scanner and communications system may be included integrally with one or more infusion pumps 22, 24, 26, and 28 in cases where a PM 50 is not used.

The patient care system 20 may be interconnected with various medical facility information systems through different means. For example, the hospital may have a main information server 56 containing patient data and drug data. In another example, the medical facility may have various individual servers, such as a pharmacy server, a physician order entry server, a patient administration server, nurse station server, and others. The patient care system 20 may be connected to one or more of these servers through various means. Hard wiring to local area networks may be in place, but RF, IR, Blue Tooth, and other wired and wireless connections may be used between the patient care system and other information systems of the facility. Information may also be exchanged with the patient care system through the use of the PDA 58. In one embodiment, the PDA may be linked to the main server 56 through wireless or other means and can become the information conduit between the patient care system and the main server.

A view of the closed front of an infusion pump module 28 is shown in FIG. 2. The pump module includes a front door 60 and a handle 62 that operate to lock the front door in a closed position and unlock and open the door for access to the internal pumping and sensing mechanisms. A display 64, such as an LED display, is located in plain view on the door in this embodiment and may be used to visually communicate various information relevant to the pump module, such as "alerting" and alarm messages. Control keys 66 exist for programming and controlling operations of the infusion pump as desired. The infusion pump module 28 also includes audio alarm equipment in the form of a speaker (not shown).

Figure 3:
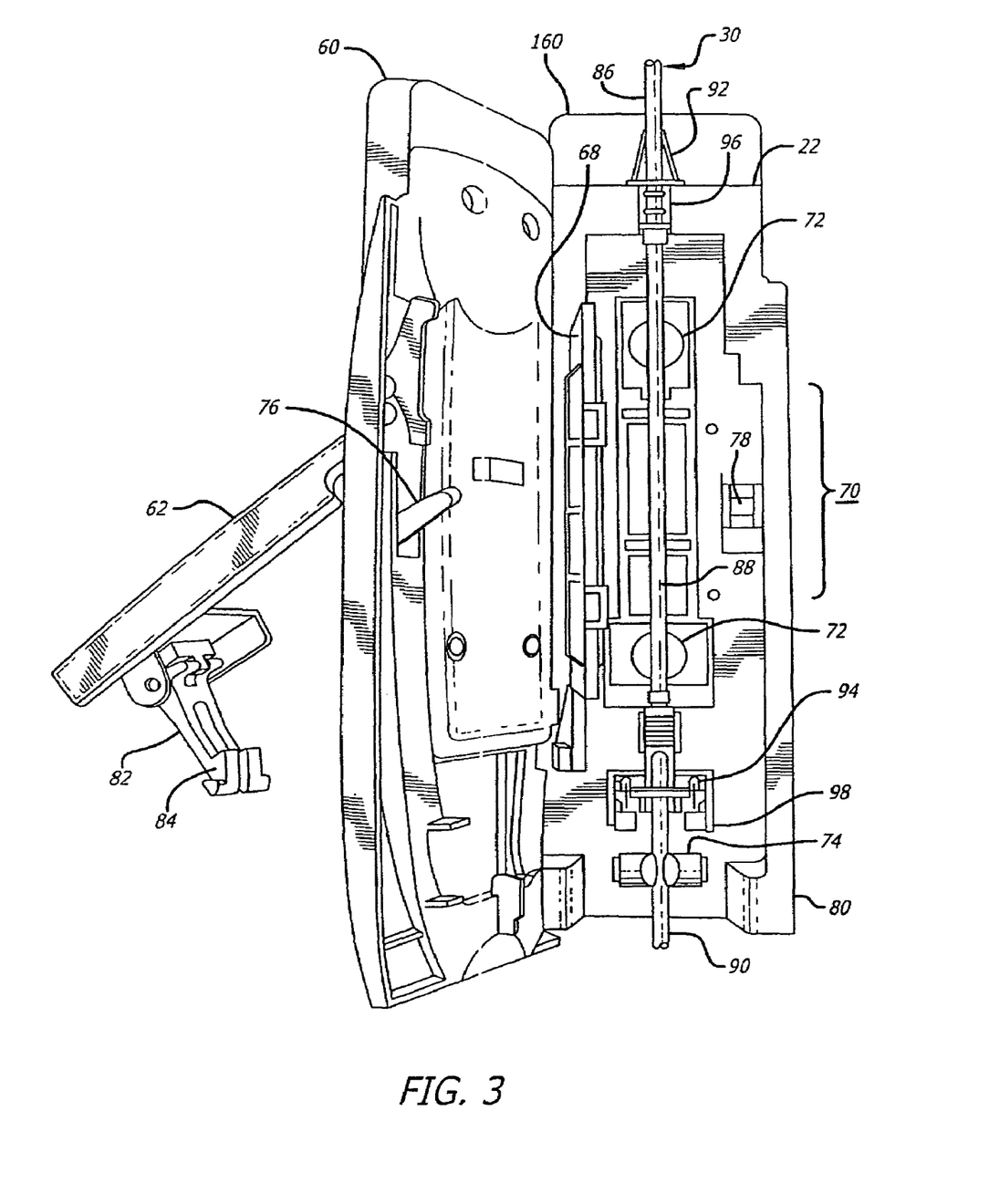
FIG. 3 is a view of one of the fluid infusion pumps of FIGS. 1 and 2 with its door in the open position and the fluid infusion channel of its respective administration set in operative engagement with the infusion pump. Also shown at the upstream end of the pump is the optics and light housing for a verification system in accordance with aspects of the invention.

Turning now to FIG. 3, the infusion pump 22 of FIGS. 1 and 2 is shown in perspective view with the front door 60 open, showing the administration set 30 in operative engagement with the pump 22. A platen 68 is mounted between the door 60 and the pumping mechanism 70. In this case, the pumping mechanism is of the linear peristaltic type. Pressure sensors 72 are included in the pump 22 both upstream and downstream of the pumping mechanism. The pump also includes an air in line sensor 74 at its downstream end. The handle 62 includes a latch arm 76 positioned to engage a yoke 78 located on the housing 80 of the pump. Engagement of the yoke by the latch arm will permit the door to remain locked in the closed position. The handle 62 also includes a sear 82 having at least one hook 84 for use in controlling a flow stop system.

The fluid administration set 30 comprises a fluid infusion conduit extending from the fluid source 38 (FIG. 1) to the patient 48, that includes an upstream tube 86, a pumping segment 88, and a downstream tube 90. Another component of the administration set tubing 30 is an upstream fitment 92 that connects the upstream tube 86 and the pumping segment 88. Similarly, a flow stop 94 connects the pumping segment 88 and the downstream tube 90. The pumping segment 88 is mounted across the pumping mechanism 70 of the infusion pump 22 by the secure engagement of the upstream fitment 92 with an upper housing portion 96 and the engagement of the flow stop 94 with a lower flow stop bracket 98. The distance between the mounted upstream fitment and the flow stop bracket puts tension on the pumping segment 88 that, by design, tends to hold it in position over the pumping mechanism 70. When the administration set 30 is engaged with the pump 22, the pumping segment 88 is positioned against the pumping mechanism 70 and held in place by the platen 68 which swings into operating position as the pump module door 60 is closed.

Figure 4:
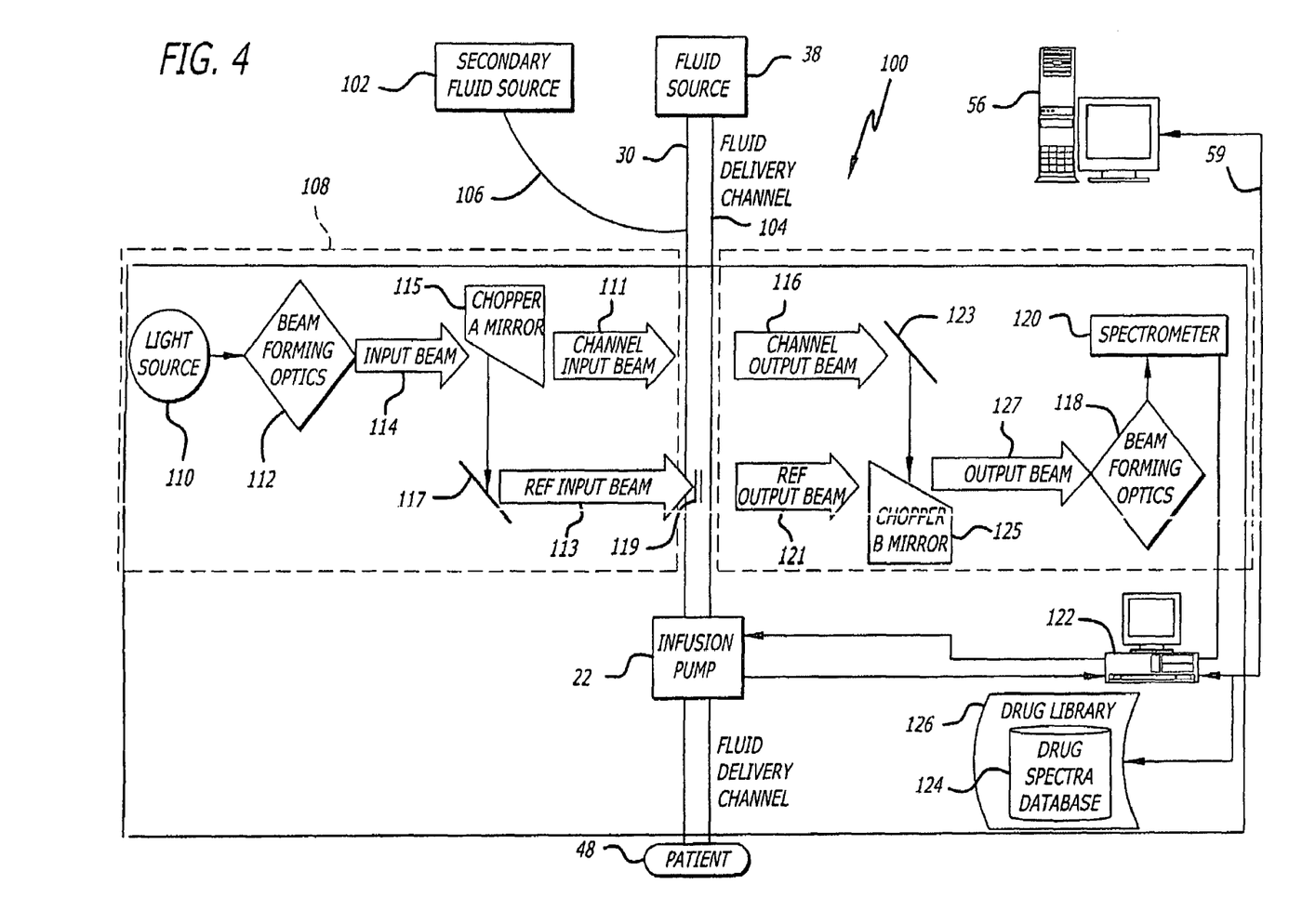
FIG. 4 is a block diagram of a medical fluid verification system and method in accordance with aspects of the invention.

Referring now to FIG. 4, a block diagram of a drug verification system 100 in accordance with aspects of the invention is shown connected to a patient 48. A fluid source 38, which may take various forms, is connected to the patient 48 through a fluid administration set 30, which is referred to as a fluid delivery "channel" herein. The designation "channel" is particularly appropriate in reference to the pump system shown in FIG. 1 because there are four lines or "channels" of drugs being administered to the same patient simultaneously. In the embodiment of FIG. 4, the fluid delivery channel 30 connecting the fluid source 38 to the patient 48 is implemented by an infusion pump 22 that is used to precisely control the rate of infusion of the drug or drugs of the fluid source into the patient. However, also shown is a secondary fluid supply 102 that is also connected to the fluid channel 30 through a Y-site device 104. It is also typical in the administration of medical fluid to a patient that a secondary infusion be conducted in which a first and second drug may be administered sequentially using the same infusion channel. Such an arrangement is shown in FIG. 4 in which the secondary fluid supply 102 is connected through a secondary fluid line 106 to the channel 30 through the Y-site device 104. As is well known, the secondary fluid source would be elevated above the primary fluid source so that only one fluid flows through the channel at once. A check valve or other device would normally be used to control the fluids in the channel 30 although such details well known to those skilled in the art have not been included so that clarity of FIG. 4 may be preserved.

In accordance with the background discussed above, it is desirable to verify the actual composition of the fluid being infused into the patient. Such verification would be desirable regardless of the means used to effect infusion, whether it is an infusion pump, mere gravity, or other means. An example of the use of an infusion pump is provided in the specification and drawings herein; however, it should be recognized that other means may be used. Although, the embodiment described and shown herein positions the sensor of the fluid verification system upstream of the infusion pump, verification may occur at another location or locations. For example, a sensor of the fluid verification system may be located downstream of the infusion pump. In the case of a gravity feed system, the fluid verification system sensor may be located anywhere along the fluid infusion channel. In the case of a secondary infusion through the same channel, it would be desirable to locate the sensor of the fluid verification system downstream of the point where the secondary fluid is added to the fluid channel, such as is shown in FIG. 4.

The process of verifying pharmaceuticals in an infusion pumping system described above begins with an expected drug selection and drug concentration input to a processor 122 associate with the pumping system 22 by any of the methods described, i.e., key press entry, PDA, RFID, or any other means employed by the technology in the system. The drug selection triggers the processor to access the matching drug spectral data from a drug spectra data base 124. The processor waits for a response of the actual measured drug spectral data, determining if a match or mismatch exists between the expected drug spectral patterns of the drug library selection and the actual drug reading from the fluid infusion channel. Although shown as local to the pump 22 in FIG. 4, the processor and the data base of drug spectral data may be located other than proximate the pump. Further, the data base of drug spectral data may be located remotely from the processor. For example, in the case of the Medley™ Point-Of-Care System, the processor may be located in the programming module 50, FIG. 1, or even elsewhere. The data base of drug spectral data may be located at the hospital server 56 area and the programming module 50 will communicate directly with it. In another case, both the processor and the data base of drug spectral data may be located in a PDA 58. Other arrangements are possible.

Detection of fluid in channels "one" through "four" takes place with light energy transmitted through fluids and interacting with the molecules of the fluids. The transmitted light energy at any wavelength may variously be attenuated, frequency shifted, or otherwise influenced by those interactions. Optical analysis means, such as dispersive, Fourier Transform Infrared (FTIR), and Raman spectroscopy, may be used to detect the characteristics of the received optical beams. The spectrum and related data of the fluid so obtained is used to detect the drug or drugs of interest. The light source and other optical and electronic components are selected to produce the required spectral resolution characteristics for differentiating drugs in the infusion channel by comparison to a prerecorded drug library.

In one embodiment, an input beam of monochromatic or heterochromatic light is caused to impinge upon the fluid delivery channel such that in traversing the delivery channel the beam passes through the medical fluid contained therein. After having passed through the medical fluid, the light energy, now called an output beam, is then optically analyzed as described above. The input and output beams may be conducted by optical fibers or other suitable optical means such that the light transmitted through the fluid is brought to the spectrometer and detection means contained therein. Both sides of the channel include beam directing apparatus in this embodiment, although other arrangements are possible. This described optical detection system is indicated generally in FIG. 4 in dashed lines and is given numeral 108. The performance of such a detection system 108 may be improved by means known to those skilled in the art, such as stray light baffling, optical filtering, the use of confocal apertures, and heterodyne detection techniques.

With continuing reference to FIG. 4, a light source 110 is coupled to input beam-forming optics 112, such as a lens and optical fiber or fibers, to provide a suitable main input beam 114 of light. The main input beam is alternately directed by a chopper 115 to create two separate intermittent beams 111 and 113. One beam, i.e., the channel input beam, is directed at the fluid channel 30 so that the light of the channel input beam may interact with the medical fluid contents of the fluid channel. The other separate intermittent beam, i.e., the reference input beam 113, is directed by means of a mirror 117 through the channel material only, in this case, through its "fin" 119 which is shown in more detail in FIG. 6 and is described below. Proper direction of the main input beam may be accomplished by use of an optical fiber or fibers and a lens (not shown) forming part of the input beam-forming optics 112.

Once the channel input beam 111 has interacted with the contents of the fluid channel 30, a channel output beam 116 results. Likewise, once the reference input beam 113 has interacted with the material of the channel 30, a reference output beam 121 results. In this embodiment, the channel output beam 116 is redirected by the reflection of a second mirror 123. Both the channel output beam and the reference output beam are exposed to a chopper 125 that creates a main output beam 127. Output main beam-forming optics 118, such as a lens (not shown) and an optical fiber or fibers, conduct the main output beam 127 to a spectrometer 120. The reference beam output data is subtracted from the fluid spectra data. The channel output of the spectrometer is compared by a processor 122 to a drug spectra data base 124 to verify the composition of the fluid channel. Control over the progress of the infusion may be exerted by the processor as a result of the verification process. In FIG. 4, it is shown that the processor 122 is connected to the infusion pump 22 that is controlling the infusion of the medical fluid 38 to the patient 48. The medical fluid may contain a drug or drugs to be infused to the patient. As an example, if the processor 122 were to determine that the drug detected in the fluid channel 30 is inconsistent with the drug expected to be there, the processor initiates a signal to the pump 22 to cease the infusion and provide a signal, such as an alarm.

The light source 110 may comprise an infrared ("IR") energy source or a tungsten energy source or other narrowband or broadband light. Preferably, the light source generates non destructive light that will not alter the chemical composition of the medical fluid undergoing verification. In one embodiment, the light source is selected to generate light that encompasses a wavelength range that interacts with the contents of the fluid in the channel 30. In particular, the light source may be selected so as to produce light in a wavelength range or spectrum with which the possible contents of the fluid channel have distinctive light absorption or reflection properties. In one embodiment, the light source produces appropriate IR energy in wavelength bands suitable to provide distinctive spectral data on absorption or transmittance behavior of the possible fluids in the channel 30 in order to verify the fluid composition. Many medical drugs have distinctive light absorption or transmittance properties in specific wavelength bands in the IR spectrum.

In another embodiment, the light source 110 produces light of a single wavelength that interacts with the contents of the medical fluid undergoing verification by Raman spectroscopy. In one embodiment, the light is a monochromatic beam of visible light suitable to provide distinctive Raman spectral data for the possible fluids within the channel 30. Upon interaction with the fluid contents of the channel, the monochromatic light undergoes excitation with a shift in electrons, known as the Raman Effect. The resulting shifts can then be analyzed to verify the chemical makeup of the fluid.

The output beam-forming optics 118 may also include a light dispersing device, such as a diffraction grating, that separates the output light into its spectrum of individual wavelengths for processing and verification. Alternatively, the light dispersing device may be an interferometer. The distributed light impinges on a sensor that may take the form of a photo detector array such as a CCD matrix or other light sensitive device that generates spectral data signals representative of the wavelength strength of the light impinging on its individual cells. In the case of FIG. 4, the sensor is termed a spectrometer 120.

The spectrometer 120 communicates with the processor 122 sending the spectral data signals of the actual fluid contents of the channel 30 to the processor for verification. The processor has many functions one of which is to verify that the actual fluid contents of the channel 30, based on the received spectral data signals are the expected fluid contents of the fluid channel 30. The processor may convert analog spectral data signals to digital data for the verification. To perform the verification function, the processor matches, or attempts to match, the spectral data produced by the spectrometer with drug spectral data retrieved from a drug spectra data base 124. In one embodiment, the clinician has entered the identification of the expected drug contents into the patient case system 20 via an input device, such as the control keys 54 (FIG. 2) or a bar code scanner that reads a bar code label applied to the fluid source 38 by the pharmacist, or by means of a PDA 58 (FIG. 1) or through other means, such as the RFID tag described above, or other device or devices. This may be done at the time the nurse loads the administration set 30 attached to the fluid source 38 into the pump 22.

The above identification means are examples only. Other means may be used to identify the expected composition of the fluid source, such as the nurse selecting a drug or drug combination from a scrolling list on the front panel of the PM 50 (FIG. 2). In this embodiment, the PM may first access a drug library 126 through the processor 122 and then display in the scrolling list only those drugs that are present in the drug library. This drug selection made by the nurse or by other means then indicates to the processor what drug is expected to exist in the fluid contents of the channel. In another embodiment, identical drug libraries may exist in the infusion pump 22 and the processor 122. In yet another embodiment, a drug library may exist in the pump and is used by the processor 122. Additionally, the drug library 126 may also be configured to be periodically updated through the communications system 59 using an external device such as a computer 56 running appropriate software or through the PDA 58 (FIG. 1) or by other means. Other means may be used to indicate to the processor 122 what drug or drugs are expected in the fluid contents. For example, a main server may communicate directly with the PM 50 or the processor 122 to indicate the identification of the drug or drugs expected to be in the fluid channel. The above examples are not meant to be exclusive of others and in fact, other arrangements may be used.

As a more general discussion, clinician-generated input prior to the commencement of infusion triggers the initial drug data comparison and verification activities. In one embodiment, detection may continue on a periodic basis for the remainder of the infusion.

The output from the optical detection system 108 comprises data signals that are transmitted to the processor 122 for analysis. The processor's main functions are to gather and interpret:

1. user-entered drug selection spectral data patterns identified from memory's drug library 126, selections matched to unique spectral data from the drug spectra data base 124;

2. diluent ratio in producing expected spectral data;

3. drug spectra as detected by the optical detection system 108 and translate it to a form usable with step 1 above; and 4. spectral data of the material comprising the fluid channel 30 (discussed below).

Further, the processor:

5. wall material spectral data as unique from channel spectral data to isolate the spectral characteristics caused by the drugs alone (discussed below); and 6. attempts to match no. 5 with no. 1 above; i.e., drug spectra as identified by user entry with the drug spectra determined by real-time measurement.

To re-state the above, the processor 122 compares the data obtained by the spectroscopy of the fluid contained in the infusion channel 30 with the stored data 124 for the drug it expects to see in that channel. In this embodiment, the processor may first access the drug spectra data base 124, as directed by customer protocol. When the processor 122 is informed that a drug combination should exist in the channel, an algorithm would be used to determine the appropriate spectrum. The drug spectra data base 124 may contain algorithms to permit the combination of stored spectra for a set of drugs, compounds, and combinations of drugs that represent all possible compositions within the fluid channel. The drug spectra data base would include, for example, the spectra associated with pure or compound drugs, such as sodium chloride or dopamine, and might synthesize the spectra of combinations of these fluids. The expected composition of the fluid channel 30 is identified to the data processor by the user interaction, for example during pump programming. The processor compares expected composition with the sensed drug obtained real-time from the channel's lumen contents. The processor compares the expected and measured spectra and determines the degree of correlation between them. Comparisons may be made on a peak-by-peak basis, by autocorrelation, or by other means known to those skilled in the art. The processor 122 outputs the verification results by providing a signal, indicating that either a match or no match occurred between the expected and real time sensed signals.

In another embodiment, rather than having algorithms to synthesize spectra of combinations of drugs, the data base 124 may simply contain spectra of all possible pure drugs and combinations of drugs. Since in one case the identification of the drug or drugs in the fluid channel involves a selection from a predetermined list, the choices facing the nurse or the medical facility are limited. Therefore, spectra of all of these limited choices may be installed in the date base 124.

In another aspect, the drug spectra data base 124 may also contain light spectrum patterns of additional agents added to a primary infusion. Such situations could occur where a primary infusion of dextrose is occurring and the nurse adds an additional medicine through an injection port of the channel downstream of the primary, but upstream of the pump, such as is shown in FIG. 4. The drug spectra data base may contain spectra for each of the possible secondary drugs and for combinations of secondary drugs with primary drugs. The data base 124 would thus include spectra that represent all possible compositions of the channel 30 with or without any possible secondary drugs.

An overview of a procedure using the system described in one embodiment comprises:

1. The clinician identifies the expected composition of the fluid source to be infused;

2. The drug source 38 is mounted, the drug channel 30 primed, and the drug channel is properly mounted in the pump 22 in the usual manner;

3. The pump is programmed for the infusion, including the identification of the drug anticipated to be in the fluid container;

4. The pump is activated;

5. Upon activation, but prior to beginning the infusion, the input light beam 114 is transmitted through the fluid delivery channel, and the detection means 108 described in this application are employed;

6. The spectra obtained from the fluid composition in the infusion channel are compared to the stored spectra 124 of the fluid expected to be in the infusion channel;

7. If the analysis confirms that the spectra are sufficiently similar to conclude that the fluid in the infusion channel is in-fact the drug anticipated, the infusion is started. An appropriate message may appear on a display to inform the user of the match; and 8. If the comparison indicates the fluid in the infusion channel does not sufficiently match the expected drug, an alarm or warning display and signal may be activated. User intervention is required to begin the infusion in this case.

The infusion pump module 22 shown in FIG. 1 may be used as the infusion pump of FIG. 4, while the PM 50 of FIG. 2 may comprise the processor 122. The drug spectra data base 124 and drug library 126 may be located in the PM 50 as well or in other embodiments, may be located in the infusion pump or even more remotely from the infusion pump and the PM such as in a nurse station server or elsewhere. The communications link 59 may be used in conjunction with a drug delivery control system in the PM 50 to allow the clinical institution through a server 56, or other means, to set a drug library into memory 126 of the PM that, as an example, includes drug concentration, dose limits, and systems configuration parameters for drugs, patient weights, and hospital wards. Further details on such a drug library system can be found in U.S. Pat. No. 5,681,285 to Ford, incorporated herein by reference. Other means may be used to set a drug into memory, such as a wireless connection with a communications device, such as a PDA 58 for example (FIG. 1), or the drug library may be loadable through different type of processor, such as a portable computer as shown in U.S. Pat. No. 6,269,340 to Ford, incorporated herein by reference. Although two memories 124 and 126 are shown (FIG. 4), they may actually reside in the same physical memory.

The drug library 126 may include limits set by the clinical institution for each drug of the library. Such limits may take the form of maximum and minimum dosages for each drug which may be made dependent on patient factors or other factors associated with delivery of the drug. For example, the dosage limits may vary depending on the weight of the patient or body surface area ("BSA"), depending on the unit or ward of the medical institution in which the drug is being used (for example neonatal care unit (NCU), the intensive care unit (ICU), etc.), and depending on other factors. An alarm may be provided if the nurse sets the pump to operate outside the range between the limits for a particular drug. In some cases, the alarm may be overridden and in other cases it may not. The medical facility may establish "soft" limits for each drug, which may be overridden by the nurse, and "hard" limits which may not. In either case where a limit is exceeded, a pump 22 data log or data log in the PM 50 or other processor in communication with the infusion pump may record each such limit event for later analysis where the attempted setting is higher than the maximum or lower than the minimum dosage.

Figure 5:
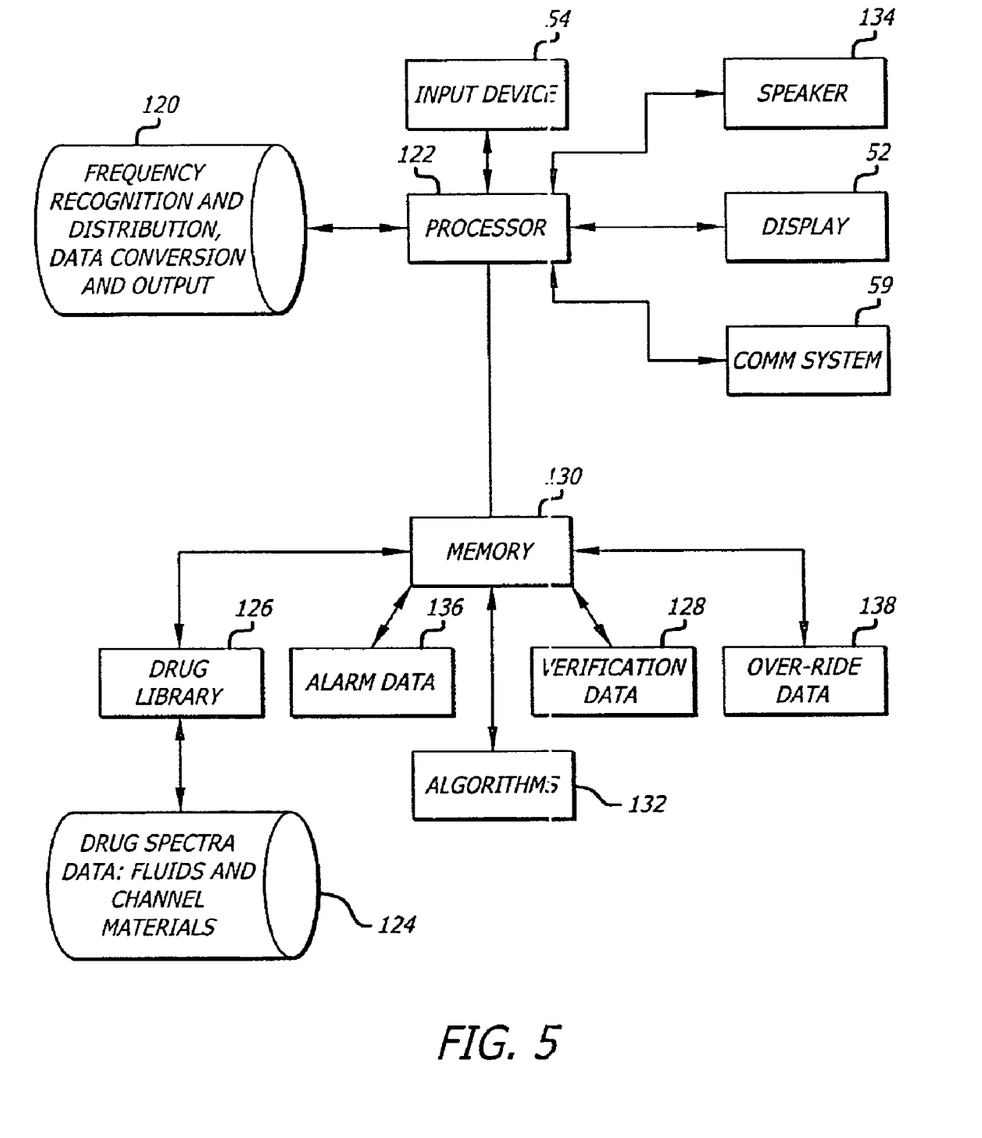
FIG. 5 is a block diagram of aspects of a system and method in accordance with the invention where the comparison is made between spectral data of the contents of a fluid channel and stored spectral data of the expected fluid composition of a channel. Also illustrated are alarm implementations and stored data bases having relevance to aspects of the invention.

The analysis of spectral data is shown in further detail in the block diagram of FIG. 5. The expected composition of the fluid source is identified to the processor 122 through an input device, such as the keys 54 of the PM or from a remote location through a communications link 59 and as otherwise described above. Data of the expected composition is accessed from the drug spectra data base 124 of the memory 130. The processor 122 then compares the data base drug spectrum to the drug spectrum received from the spectrometer 120 representing the fluid composition of a channel under analysis. Comparison techniques that may be used in matching the data have been described above and algorithms used for comparison and matching are stored in the algorithm portion 132 of the memory 130, or elsewhere. In the event that the comparison by the processor indicates that the spectrum of the actual fluid composition of the channel does not match the spectrum of the expected fluid composition of the channel, the processor may provide an audio alarm signal by means of the speaker 134, and/or a visual alarm by means of the screen 52 on the PM or other screen, and/or remote alarms through a communication link such as 59 or other link. The memory may store all alarm and alarm-related data 136 including any overrides 138 of alarms occurring with this medical instrument. Such stored alarm and override data may be processed by the processor 122 or downloaded to another system for analysis and reporting to medical care personnel. Uses of such data include determining if the drug limits in the drug library are suitable or if medical practices at the medical facility need adjustment. Other uses of the data can be made. Results of verification may also be stored in a memory 128.

Figure 6:
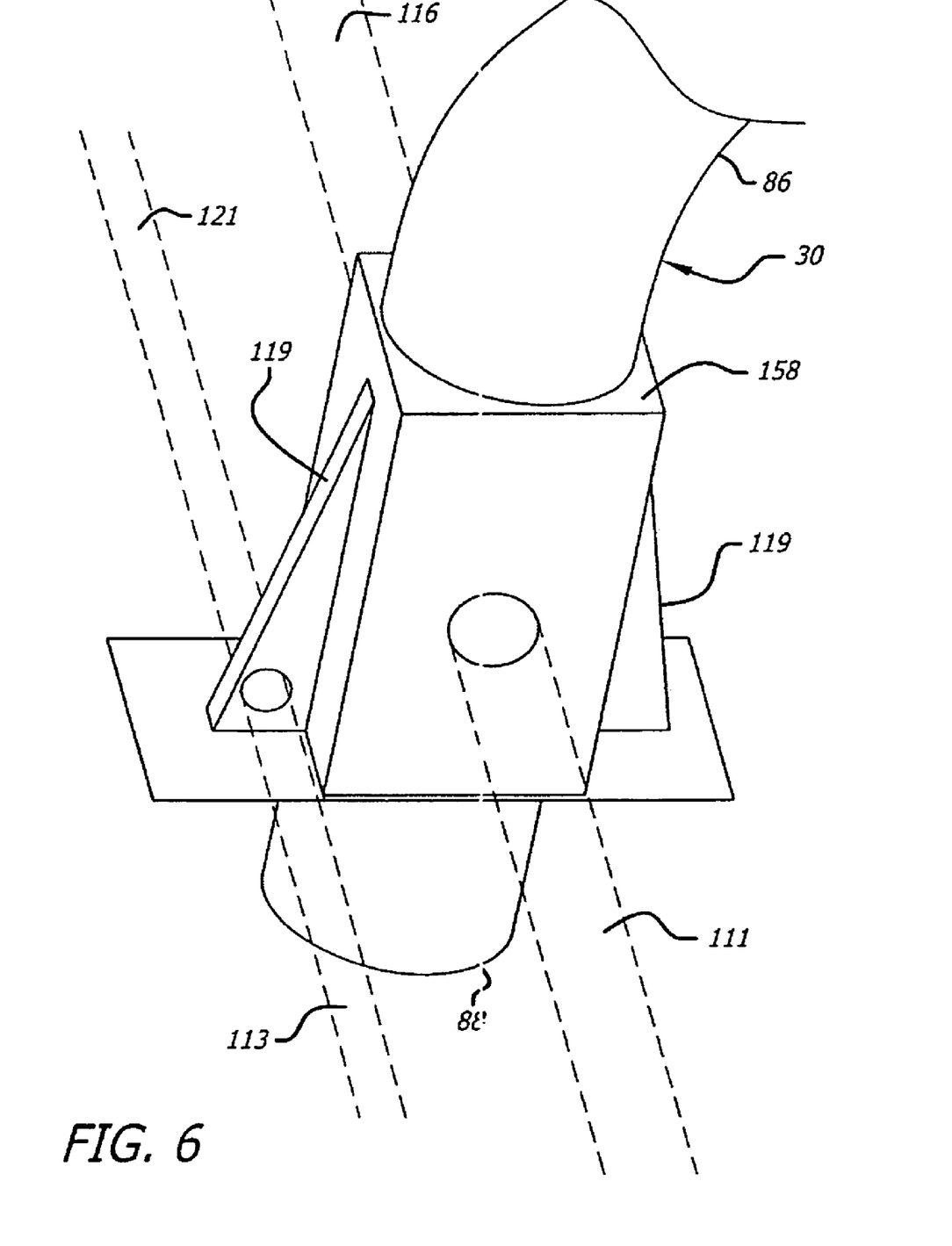
FIG. 6 is an example in perspective block view of an implementation of a fluid channel through which a light beam may be transmitted to verify the contents of the channel, the channel also having a reference portion through which a reference beam of light is transmitted to develop spectral data concerning the composition of the wall of the channel so that accuracy in verifying the channel contents may be improved.

Disclosure is now provided of an example of a mechanical implementation of a channel for use with an optical detection system 108, the channel usable with the fluid verification system and method described above. Referring now to FIG. 6, an upstream fitment 158, similar to that fitment 92 shown in FIG. 3, interconnects an upstream tube 86 and a pumping segment 88 that form parts of a fluid channel 30. The fitment 158 is shown having two fins 119, one of which is used with the reference input beam 113. The channel input beam 111 is shown as being positioned such that it extends through the approximate center of the fitment 158. After both input beams of light 111 and 113 have penetrated the fitment and exited on the far side, in this embodiment, a channel output beam 116 and a reference output beam 121 result.

As shown in FIG. 3, the fitment 92 may be used to secure the fluid channel 30 in the proper location in regard to the pump so that successful fluid verification, air-in-line sensing 74, pressure sensing 72, and mechanical pumping 70 may occur. In the embodiment of FIG. 6, the fitment 158 would replace the fitment 92 in FIG. 3. FIG. 3 also shows a housing 160 within which may be mounted various components of the fluid verification system 100. In particular, although not shown in FIG. 3, components of the optical detection system 108 may be located in the fluid verification housing 160. For example, the beam forming optics 112, the first chopper 115, first mirror 117, second mirror 123, second chopper 125 and the output beam forming optics 118 may be located in the housing 160. Additional, or fewer, of these components may be located in the housing depending on their implementation.

In another embodiment, the fluid verification system 100 could be configured to automatically compensate for the absorption and Raman spectrum of the material of the fitting 158 without an input reference beam 113 because the light absorption and Raman properties of the typical plastic materials used for fluid infusion conduits are generally well known. In this embodiment, the fluid verification system may store the data on the conduit spectrum and automatically subtract the conduit spectrum from the fluid composition spectrum during fluid analysis.

In the case where a care giver must infuse a drug that is not in the drug library 126, the verification system 100 may be placed in override and no spectral comparisons will be made, although the pump may still be operated.

In yet another embodiment where further processing capability is available, the verification system 100 may first perform the above-disclosed matching function between expected fluid composition and actual detected fluid composition. If a match does not exist, the system will indicate this fact to the care giver through the means discussed above. The care giver may then have the option of requesting the system to attempt to identify the actual composition of the fluid conduit. The system will then attempt to match the spectrum of the actual detected fluid composition to a spectrum or spectra in the drug spectra data base 124 to identify the fluid composition. If identification is successful, the identity of the drug may be indicated on the display 52, communicated verbally 134, or otherwise communicated to the care giver, or to others. In another aspect, the system may also be configured to permit the care giver to directly request the system 100 to compare the spectra of selected drugs from the drug library 126 against the spectrum of the actual detected fluid conduit composition. Through this latter means, if identification is successful, the care giver may then be able to determine that the fluid administration set from one drug was mistakenly installed in the infusion pump under verification and can then more quickly move the administration set to the correct pump.

In another embodiment where a system such as that shown in FIGS. 1 and 2 is used in which a PM 50 controls multiple infusion pump modules 22, 24, 26, and 28, and an identification of the actual drug in the administration set is successful, the PM may simply reprogram that infusion module for the correct drug either automatically or at the option of the care giver. With a system such as this, the necessary pumping program may be entered into the PM when the bag of medicament is first received, and the PM will properly program the specific infusion pump module with that program once the module detects the presence of the administration set with that particular medicament in it. Other variations on this procedure are possible.

In the case of a secondary infusion followed or preceded by a primary infusion as shown in FIG. 1, it would be desirable to check the composition of the fluid channel downstream of the Y-site 104 multiple times to verify both the contents of the primary fluid and the secondary fluid being infused to the patient. In such cases the infusion channel may contain only one or the other drug at a particular time. Thus, in addition to verifying the contents of the infusion channel prior to the start of infusion, it would be a desirable feature to have the detection means periodically monitor the contents of the fluid channel 30 on an ongoing basis. Such continuous monitoring would also permit the system to determine when the secondary infusion is complete because the spectrum of the fluid contents of the fluid channel will change. Automating the drug verification system 100 would permit the processor 122 of the system to switch the pumping parameters of the infusion pump 22 to those required for the primary infusion or the secondary infusion at precisely the correct time.

From the foregoing, it will be appreciated that the fluid verification system in accordance with the principles of the invention provides an effective system to determine the contents of a medical fluid in a fluid infusion line in order to ensure infusion of the proper drug. Such a system and method can also permit more automated handling of fluid infusions.

Although specific embodiments of the invention have been described and illustrated it is clear that the invention is susceptible to modifications and embodiments within the ability of those skilled in the art, and without the exercise of the inventive faculty. Thus, it should be understood that various changes in form, detail, and application of the present invention may be made without departing from the spirit and scope of the invention.

We claim:

1. An apparatus for verifying the composition of a fluid contained within a fluid infusion channel, wherein the channel includes a channel wall and an interior through which the fluid is conducted, the apparatus comprising:
    a source of light located and configured so as to direct light through the fluid contained within the channel;
    a light sensor located so as to receive the light that was directed through the fluid contained within the channel after it has passed through the fluid, the light sensor providing light sensor signals representative of spectral data of the actual composition of the fluid contained within the channel; and
    a processor that is adapted to compare the spectral data of the actual composition of the fluid with spectral data of an expected composition of the fluid contained within the channel, and further comprising predetermined spectral data representative of the composition of the channel wall;
    wherein the processor is further adapted to adjust the spectral data of the actual composition of the fluid within the channel with the predetermined spectral data representative of the channel wall.

2. The apparatus of claim 1 further comprising a memory in which is stored the spectral data of the expected composition of the fluid contained within the channel;
    wherein the processor accesses the memory to obtain the spectral data of the expected composition of the fluid contained within the channel.

3. The apparatus of claim 1 further comprising an input device with which an indication of the expected composition of the fluid is input to the processor.

4. The apparatus of claim 1 wherein the channel is operated on by a pumping mechanism of an infusion pump;
    wherein the source of light and the light sensor are disposed at locations on the infusion pump upstream from the pumping mechanism.

5. An apparatus for verifying the composition of a fluid contained within a fluid infusion channel, wherein the channel includes a channel wall and an interior through which the fluid is conducted, the apparatus comprising:
    a source of light located and configured so as to direct light through the fluid contained within the channel;
    a light sensor located so as to receive the light that was directed through the fluid contained within the channel after it has passed through the fluid, the light sensor providing light sensor signals representative of spectral data of the actual composition of the fluid contained within the channel;
    a processor that is adapted to compare the spectral data of the actual composition of the fluid with spectral data of an expected composition of the fluid contained within the channel; and
    a reference element having approximately the same composition as the composition of the channel wall;
    a reference light located and configured so that it directs light through the reference element; and
    means for sensing the reference light that was directed through the reference element after it has passed through the reference element, the reference light sensor providing light sensor signals representative of spectral data of the actual composition of the reference element;
    wherein the processor is further adapted to adjust the spectral data of the actual composition of the fluid within the channel with the spectral data of the actual composition of the reference element.

6. The apparatus of claim 5 wherein the reference light is generated by the source of light.

7. The apparatus of claim 5 wherein the means for sensing the reference light comprise the light sensor.

8. The apparatus of claim 7 further comprising a first beam forming device that is configured to form the reference light as a separate reference beam from the light source and is further configured so as to direct the reference beam through the reference element; and
    wherein the light sensor is located so as to receive the reference beam after it has passed through the reference element and provide sensor signals representative of the reference element spectral data.

9. The apparatus of claim 8 wherein the light sensor comprises a second beam forming device configured so as to receive the reference beam after it has passed through the reference element and provide the reference beam to the light sensor.

10. The apparatus of claim 1 further comprising:
    a memory in which is stored a plurality of spectra data representative of possible expected fluid compositions contained within the channel;
    an input device with which the expected composition of the fluid contained within the fluid channel is input to the processor;

wherein in response to the input device the processor accesses the memory to obtain the spectral data of the expected composition of the fluid contained within the channel.

11. The apparatus of claim 10 wherein the processor is adapted to access additional spectra in the memory in the event that the spectral data of the expected composition does not match the spectral data of the actual composition and make a further comparison of spectral data from the memory to the spectral data of the actual composition, and in the event that a match is detected, indicate the spectral data that matched.

12. The apparatus of claim 10 wherein the processor is further adapted to synthesize spectral data for the expected fluid composition from spectral data in the memory.

13. The apparatus of claim 1 wherein the processor is further adapted to provide an alarm signal in the event that the spectral data of the actual composition does not match the spectral data of the expected composition.

14. The apparatus of claim 4 wherein the processor controls the pumping mechanism;
the processor is further adapted to prevent the pumping mechanism from operating in the event that the spectral data of the actual composition does not match the spectral data of the expected composition.

15. The apparatus of claim 14 wherein the processor is further adapted to permit an operator of the pump to override the processor in the event that the spectra do not match.

16. The apparatus of claim 15 further comprising a memory;
wherein the processor is further adapted to store in the memory an override of the processor and fluid verification data.

17. The apparatus of claim 16 wherein the processor is further adapted to communicate with a hospital server located remotely from the processor, events relating to comparisons of spectral data.

18. The apparatus of claim 1 further comprising a reader device in communication with the processor adapted to read an identification device related to the fluid, the identification device including an indication of expected composition of the fluid.

19. The apparatus of claim 18 wherein the identification device contains spectral data of the expected composition of the fluid.

20. The apparatus of claim 18 wherein the identification device contains an indication of the expected fluid composition and the processor is adapted to retrieve spectral data consistent with the expected fluid composition.

21. The apparatus of claim 18 wherein the identification device comprises a bar code and the reader comprises a bar code scanner.

22. The apparatus of claim 18 wherein the identification device comprises an RFID tag and the reader comprises an RFID reader.

23. The apparatus of claim 19 wherein the identification device comprises a wireless information device and the reader comprises a compatible reader of the wireless information device.

24. A method for verifying the composition of a fluid contained within a fluid infusion channel, wherein the channel includes a channel wall and an interior through which the fluid is conducted, the method comprising:
directing light through the fluid contained within the channel;
sensing the light that was directed through the fluid contained within the channel after it has passed through the fluid and providing light sensor signals representative of spectral data of the actual composition of the fluid contained within the channel; and
comparing the spectral data of the actual composition of the fluid with spectral data of an expected composition of the fluid contained within the channel, further comprising receiving predetermined spectral data representative of the expected composition of the channel wall;
adjusting the spectral data of the actual composition of the fluid within the channel with the predetermined spectral data representative of the channel wall; and
wherein when the adjusted spectral data of the actual composition of the fluid within the channel does not match the expected composition of the fluid contained within the channel, initiating a signal indicating that the actual composition of the fluid within the channel is inconsistent with the expected composition of the fluid contained within the channel.

25. The method of claim 24 further comprising:
storing the spectral data of the expected composition of the fluid contained within the channel in a memory;
accessing the memory to obtain the spectral data of the expected composition of the fluid contained within the channel.

26. A method for verifying the composition of a fluid contained within a fluid infusion channel, wherein the channel includes a channel wall and an interior through which the fluid is conducted, the method comprising:
directing light through the fluid contained within the channel;
sensing the light that was directed through the fluid contained within the channel after it has passed through the fluid and providing light sensor signals representative of spectral data of the actual composition of the fluid contained within the channel; and
comparing the spectral data of the actual composition of the fluid with spectral data of an expected composition of the fluid contained within the channel, further comprising:
directing light through a reference element, the reference element having approximately the same composition as the composition of the channel wall;
receiving light that was directed through the reference element after it has passed through the reference element, the received light being representative of spectral data of the actual composition of the reference element;
adjusting the spectral data of the actual composition of the fluid within the channel with the spectral data of the actual composition of the reference element; and
wherein when the adjusted spectral data of the actual composition of the fluid within the channel does not match the expected composition of the fluid contained within the channel, initiating a signal indicating that the actual composition of the fluid within the channel is inconsistent with the expected composition of the fluid contained within the channel.

27. The method of claim 24 further comprising:
storing a plurality of spectral data of possible expected fluid compositions contained within the channel;
inputting the expected composition of the fluid contained within the fluid channel;
accessing the spectral data of the expected composition of the fluid contained within the channel from the plurality of spectral data.

28. The method of claim 27 further comprising accessing additional spectral data in the event that the spectral data of the expected composition does not match the spectral data of the actual composition and further comparing spectral data to the spectral data of the actual composition, and in the event that a match is detected, indicating the spectral data that matched.

29. The method of claim 27 Further comprising synthesizing spectral data for the expected fluid composition from spectral data.

30. The method of claim 24 wherein the signal is an alarm.

31. The method of claim 24 further comprising reading an identification device related to the fluid, the identification device including an indication of expected composition of the fluid.

32. The method of claim 31 further comprising reading an identitication device that contains spectral data of the expected composition of the fluid.

33. The method of claim 31 further comprising reading a bar code identification device with a bar code scanner.

34. The method of claim 31 further comprising reading an RFID tag with an RFID reader.

35. The method of claim 31 further comprising reading a wireless information device with a compatible wireless reader.

36. The method of claim 24, wherein the signal is a control signal to cease infusion.

* * * * *